United States Patent [19]

Inamoto et al.

[11] 4,038,333

[45] July 26, 1977

[54] TRICYCLI BREDT COMPOUND, TRICYCLO[5.3.1.0³,⁸]UNDEC-2-ENE

[75] Inventors: Yoshiaki Inamoto; Yoshiaki Fujikura; Hiroshi Ikeda; Naotake Takaishi, all of Wakayama, Japan

[73] Assignee: Kao Soap Co., Ltd., Tokyo, Japan

[21] Appl. No.: 676,704

[22] Filed: Apr. 14, 1976

[30] Foreign Application Priority Data

Apr. 28, 1975  Japan .................................. 50-51700

[51] Int. Cl.² .............................................. C07C 13/28
[52] U.S. Cl. ......................... 260/666 PY; 260/666 M; 71/127
[58] Field of Search ..................... 260/666 PY, 666 M

[56] References Cited

PUBLICATIONS

A. Krautz et al., Chemical Communications, pp. 1287–1318, 1971.

A. Krautz et al., J. Amer. Chem. Soc., 95, pp. 5662–5672, 1973.

*Primary Examiner*—Veronica O'Keefe
*Attorney, Agent, or Firm*—Blanchard, Flynn, Thiel, Boutell & Tanis

[57] ABSTRACT

Tricyclo[5.3.1.0³,⁸]undec-2-ene is novel and prepared by reacting 3-halogeno-4-homoisotwistane with a dehydrohalogenating agent.

3 Claims, No Drawings

TRICYCLI BREDT COMPOUND, TRICYCLO[5.3.1.0³,⁸]UNDEC-2-ENE

BACKGROUND OF INVENTION

1. Field of Invention

The present invention relates to a novel compound, tricyclo[5.3.1.0³,⁸]undec-2-ene of the formula (II) given below. More particularly, this invention relates to a process for preparing tricyclo[5.3.1.0³,⁸]undec-2-ene of the formula (II) by reacting a 3-halogeno-4-homoisotwistane of the formula (I) with a conventional dehydrohalogenating agent such as an alkali metal amide, an alkali metal alkoxide, an alkali metal hydroxide and an amine (for example, piperidine, pyridine and quinoline), as shown below:

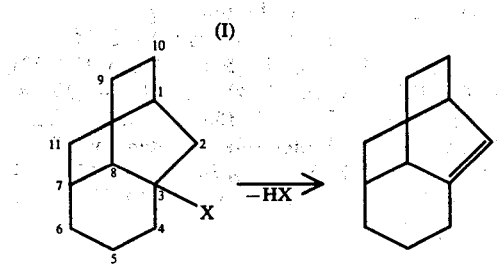

wherein X is Cl, Br or I.

Tricylo[5.3.1.0³,⁸]undec-2-ene of the formula (II) is a derivative of 4-homoisotwistane [X = H in formula (I)], and it is a very rare polycyclic compound having an bond at the bridge head position.

2. Description of Prior Art

It is known as the Bredt Rule that it is generally impossible to form an olefin bond at the bridge head position of a polycyclic hydrocarbon and such olefin is formed only under special conditions (see the survey, G. L. Buchanan, Quarterly Reviews, 1974, 3, 41).

SUMMARY OF INVENTION

According to the process of the present invention, a compound can be, contrary to the Bredt Rule, synthesized by using a conventional dehydrohalogenating agent. The process of the present invention is characterized by this feature and hence, is very valuable.

In general, the easiest process for introducing a functional group into a polycyclic hydrocarbon is achieved through a carbo-cation. As a result of our research on 4-homoisotwistane [X =H in formula (I)], it has been found that since a stable carbo-cation is formed especially at the 3-position (or the 7-position) alone, a functional group can be introduced only at the 3-position (or the 7-position). In contrast to this, according to the process of the present invention, since an olefin bond can be formed at the 2-position, it is possible to introduce a functional group even at the 2-position by utilizing the reactivity of the thus formed olefin, and simultaneously, it is possible to introduce a functional group that cannot be introduced according to the conventional process, at the 3-position.

The structure of the compound of formula (II) can be confirmed by the following facts.

In the infrared spectrum of the compound (II), absorptions are observed at 3020 cm⁻¹ (νCH=) and 1620 cm⁻¹ (νCH=C) which means that the compound is an olefin. Further, from the fact that when the compound is hydrogenated with a palladium-carbon catalyst, 4-homoisotwistane (tricyclo[5.3.1.0³,⁸]undecane, III) is formed, it has been confirmed that the carbon skeleton is not changed in the compound. When water-adding reaction is conducted with an acid as a catalyst, only 4-homoisotwistane-3-ol (IV) is formed. Accordingly, it has been confirmed that the olefin bond is formed at positions including the 3-position [see the following scheme].

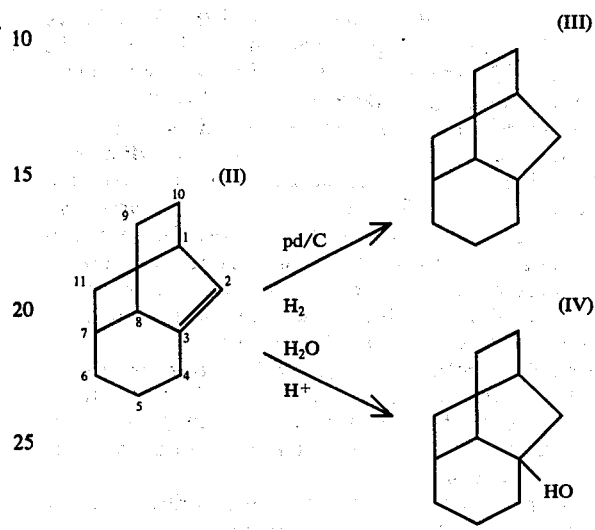

Whether the olefin bond is located at the 2-3 positions or 3-4 positions has been confirmed from the NMR spectrum of the compound of the formula (II). Namely, from the fact that the absorption of the olefinic hydrogen split into doublet (δ5.9, J = 7Hz), it is seen that one hydrogen is bonded to the β-carbon and hence, the structure (II) is supported. If it were supposed that the olefin bond is formed at the 3-4 positions, the olefinic hydrogen at the 4-position splits into triplet by the influence of the methylenic hydrogen at the 5-position, and the coupling constant should be of a smaller value in correspondence with a larger dihedral angle.

The structure of the compound of the formula (II) was determined based on the foregoing facts.

In view of the fact that derivatives of adamantane, a tricyclic hydrocarbon, have various physiological activities such as the prophylactic activity against the influenza virus of type A2 and the alleviation of the symptoms of Parkinson's disease, it is expected that 4-homoisotwistane [X = H in the formula (I)] and its derivative will have similar physiological activities and they may be used as various medicines. Accordingly, tricyclo[5.3.1.0³,⁸]undec-2-ene of the formula (II) is important as an intermediate for the synthesis of these medicines, and derivatives of this compound can be used as fiber oiling agents, extreme pressure lubricants, anticorrosion agents, lubricant additives, perfumes and agricultural medicine. The compound (II) gives 2,3-dihydroxy-4-homoisotwistane which has a chemical structure of Seychellene or Patchouli alcohol which is one of natural sesquiterpenes useful as perfume. 2,3-dihydroxy-4-homoisotwistane has an aromatic odour and is useful as a perfume. In addition, it has a physiological activity and is useful as an agricultural medicine when it is applied to the lettuce seeds in the form of a solution having a concentration of 10 to 100 ppm, preferably 30 to 70, in order to suppress germination. The dihydroxy derivative is obtained by reacting the compound (II) with osmium tetraoxide or formic acid and hydrogen peroxide and then hydrolyzing the reaction product. Therefore, the compound of the formula (II) is very important.

In practising the process of the present invention, the amount of the dehydrohalogenating agent may be an equivalent amount, but better results are generally obtained when the agent is used in an amount of at least 3 moles per mole of the compound of the formula (I). Any of polar and non-polar solvents can be used in the process of the present invention. The reaction temperature is changed depending on the kind of the solvent used, but when polar solvents such as liquid ammonia, alcohols having one to five carbon atoms, dimethylformamide and dimethylsulfoxide are employed, the reaction can be performed at lower temperatures than the reflux temperature as well as at the reflux temperature. When non-polar solvents such as hexane, benzene and toluene are employed, the reaction can be completed in a short time if the reaction is carried out at the reflux temperature of the solvent used.

As a dehydrohalogenating agent, there may be used an alkali metal amide, an alkali metal alkoxide derived from an alcohol having one to four carbon atoms and an alkali metal hydroxide, in which the alkali metal is sodium or potassium.

The present invention will now be described in detail by reference to the following Examples.

EXAMPLE 1

To a solution of 8.22 g (36 millimoles) of 3-bromo-4-homoisotwistane in 20 ml of dry toluene was added 1.4 g (36 millimoles) of sodium amide, and the mixture was stirred for 2 hours under reflux of toluene. After completion of the reaction, the reaction mixture was filtered and the filtrate was fractionally distilled to give 2.75 g (52% yield) of colorless tricyclo[5.3.1.0$^{3,8}$]undec-2-ene (boiling point of 90° to 92° C/19 mm Hg). Elementary Analysis Values:

Found: C = 88.9%, H = 11.1%; Calculated as $C_{11}H_{16}$: C = 89.1%, H = 10.9%.

IR Spectrum (neat, cm$^{-1}$): 3020 ($\nu$H—C=), 1620 ($\nu$C=C), 1450 (—CH$_2$—), 840, 820, 810

NMR Spectrum (CDCl$_3$ as a solvent, TMS as internal standard, δ): 5.9 (doublet), 2.9 - 0.9 (complicate multiplet);

Mass Spectrum, m/e (relative intensity): 148 (M+, 41), 105 (25), 94 (100), 92 (28), 91 (51), 77 (25), 66 (33), 41 (26), 18 (39).

EXAMPLE 2

To 50 ml of t-butyl alcohol was added 3.5 g (90 millimoles) of metallic potassium under nitrogen atmosphere and refluxed gently until metallic potassium was completely dissolved. A solution of 5.52 g (30 millimoles) of 3-chloro-4-homoisotwistane was added dropwise to the above solution under reflux for about 30 minutes. After completion of addition, the reaction mixture was stirred for 2 hours under reflux. Then, the reaction mixture was poured into 100 g of ice and extracted two times with 20 ml of ether. The extract was fractionally distilled to give 2.62 g (59% yield) of tricyclo[5.3.1.0$^{3,8}$]undec-2-ene.

EXAMPLE 3

A solution of 0.58 g (3.9 m mole) of tricyclo[5.3.1.0$^{3,8}$]undec-2-ene in 10 ml of dry ether was added dropwise into a solution of 1.0 g (3.9 m mol) of osmium tetraoxide in 0.7 ml of pyridine and 20 ml of dry ether over 15 min. at 0° C. The reaction was continued for further 2 hours at the same temperature. The crystalline precipitate was separated with filtration and washed with ether. To the obtained crystal (1.9 g) was added 20 ml of 10% potassium hydroxide solution containing 2.0 g of mannitol at room temperature and the reaction was effected for 2 hours. The reaction product was extracted with methylene chloride and dehydrated. After removal of methylene chloride, 0.5 g of crude crystals was obtained with yield of 70%. The crude crystals were purified by sublimation to obtain 2,3-dihydro-4-homoisotwistane having the melting point of 146° to 147° C in a sealed tube.

Elementary Analysis Values: Found: C = 72.6%, H = 9.8%; Calculated as $C_{11}H_{18}O_2$: C = 72.5%, H = 10.0%.

IR (neat) — 3300 cm$^{-1}$ (OH stretching).

Mass Spectrum m/e (relative intensity) 182 (M+, 78), 164 (39), 133 (45), 112 (34), 110 (50), 108 (39), 107 (39), 104 (40), 97 (100), 95 (43), 93 (49), 91 (61), 84 (79), 81 (44), 80 (40), 79 (80), 77 (34), 67 (58), 55 (60), 41 (82).

$^{13}$CNMR δ(ppm) (multiplet, relative intensity) 17.0 (t, 1), 18.5 (t, 1), 19.5 (t, 1), 28.8 (t, 1), 30.9 (t, 1), 32.2 (d, 1), 32.6 (d, 1), 38.9 (t, 1), 39.9 (d, 1), 69.6 (s, 0.5), 71.6 (d, 1).

$^1$HNMR δ(ppm)

0.8 – 2.2 (m, 15H)

3.2 – 3.8 (m, 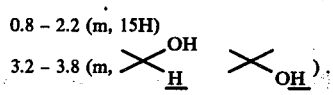 )

EXAMPLE 4

One and half gram of tricyclo[5.3.1.0$^{3,8}$]undec-2-ene was added to a mixture of 10.5 g (0.22 mol) of 98% formic acid and 1.1 g (0.011 mol) of 35% hydrogen peroxide solution and the reaction was effected for 2 hours at 65° to 70° C. Then, excess formic acid was distilled out at a reduced pressure and 15 ml of 30% potassium hydroxide aqueous solution was added, followed by reflux for 5 hours. After that, the reaction mixture was neutralized with hydrochloric acid and extracted with ether. After it was dehydrated and ether was removed, 1.3 g of white crystal was obtained with yield of 70%. The melting point and the spectrum data have been confirmed to be the same of those described in Example 3.

EXAMPLE 5

The compound obtained in Example 3 or 4, 2,3-dihydroxy-4-homoisotwistane, was dissolved in 0.05% aqueous solution of a surfactant mixture of polyoxyethylene (20) sorbitanmonooleate/sorbitanmonooleate (30/70), at various concentrations. Four milliliters of each of these solutions was placed on a plate having a diameter of 8 cm and provided thereon with a sheet of filter paper. There was a sowed a group of 50 seeds of lettuce (grade: Great Lakes No. 54) in each plate. These were cultivated at 25° C for 4 days in light (2800 Lux) and it was thereafter determined whether or not the germination rate of lettuce was suppressed with the agent. The germination rate of lettuce at each concentration of the agent is shown in the following table.

| Concentration (μg/ml) | 6.2 | 12.5 | 25 | 50 |
|---|---|---|---|---|
| Germination rate | 95 | 66 | 25 | 1 |

What is claimed is:

1. Tricyclo[5.3.1.0³,⁸]undec-2-ene

2. A process for the preparation of tricyclo[5.3.1.0³,⁸]undec-2-ene having the formula (II):

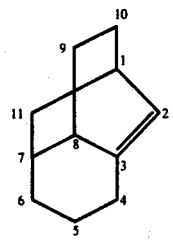

(II)

which comprises reacting a 3-halogeno-4-homoisotwistane having the formula (I):

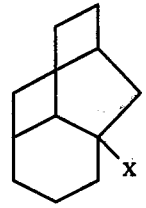

wherein X is Cl, Br or I, with a dehydrohalogenating agent in a solvent.

3. A process as claimed in claim 2, in which said dehydrohalogenating agent is selected from the group consisting of an alkali metal amide, an alkali metal alkoxide derived from an alcohol having one to four carbon atoms and an alkali metal hydroxide, in which the alkali metal is sodium or potassium.

* * * * *